United States Patent [19]

Shapiro

[11] Patent Number: 5,084,026

[45] Date of Patent: Jan. 28, 1992

[54] INTRAVENOUS APPARATUS HOLDER

[76] Inventor: Robert A. Shapiro, 133 Clapp Rd., Scituate, Mass. 02066

[21] Appl. No.: 379,989

[22] Filed: Jul. 14, 1989

[51] Int. Cl.⁵ .............................................. A61M 5/00
[52] U.S. Cl. ..................................... 604/179; 604/174; 128/DIG. 26; 128/DIG. 15
[58] Field of Search ........................ 604/174, 177–180; 128/DIG. 16, DIG. 15

[56] References Cited

U.S. PATENT DOCUMENTS

| | | | |
|---|---|---|---|
| 2,449,882 | 9/1948 | Daniels | 128/DIG. 26 |
| 2,533,961 | 12/1950 | Rousseau et al. | 604/174 |
| 3,167,972 | 1/1965 | Stone et al. | 128/DIG. 26 |
| 3,760,811 | 9/1973 | Andrew | 128/DIG. 26 |
| 3,812,851 | 5/1974 | Rodriguez | 604/179 X |
| 4,193,174 | 3/1980 | Stephens | 128/DIG. 26 |
| 4,250,880 | 2/1981 | Gordon | 604/180 |
| 4,360,025 | 11/1982 | Edwards | 604/180 |
| 4,397,647 | 8/1983 | Gordon | 604/180 |
| 4,416,664 | 11/1983 | Womack | 604/179 |
| 4,453,933 | 6/1984 | Speaker | 604/179 |
| 4,498,903 | 2/1985 | Mathew | 604/179 |
| 4,516,293 | 5/1985 | Beran | 128/DIG. 26 |
| 4,585,443 | 4/1986 | Kaufman | 604/179 |
| 4,711,636 | 12/1987 | Bierman | 128/DIG. 26 |
| 4,874,380 | 10/1989 | Hesketh | 128/DIG. 26 |

Primary Examiner—Stephen C. Pellegrino
Assistant Examiner—Ralph A. Lelois
Attorney, Agent, or Firm—John P. McGonagle

[57] ABSTRACT

An anchor pad which has straps associated therewith for securing the pad to the arm, leg or the like of a patient. Attached to the top face of the pad are two latch arrangements for adjustable holding the tubing and needle sections of an intravenous apparatus in place. In one version of the invention, the pad's under face has adhesive applied thereto.

11 Claims, 5 Drawing Sheets

INTRAVENOUS APPARATUS HOLDER

BACKGROUND OF THE INVENTION

This invention relates generally to devices for use in feeding patients intravenously or for analogous purposes such as blood transfusions, and more particularly to improvements in holders for intravenous apparatus.

In the use of an intravenous needle which is attached to the end of a flexible tubing in giving intravenous medication, blood plasma, anesthesia, and the like, the tubing which has some weight, tends to displace the needle and interferes with the proper operation of the apparatus.

Heretofore, the intravenous feeding of patients and the like required that the needle, flow tube and coupling be attached to the patient by adhesive tape to prevent it from decoupling, twisting and/or pulling out of the vein. This has been the conventional practice for a number of years. However, this practice is often unsatisfactory from a patient discomfort point of view and from a functional point of view.

Adhesive tape is difficult to remove from the patient without causing discomfort. The use of adhesive tape results in the pressure application of the base of the needle and tube coupling into the flesh of the patient which not only may prove uncomfortable, but in some cases the flesh may become bruised. When the adhesive tape is removed, arm hair may also be inadvertently removed. Use of adhesive tape over a lengthy period of time will cause tissue breakdown and other injuries to the soft tissues of the arm such as to the nerve network and various vessels in the skin. The use of adhesive tape may also lead to functional problems, i.e., inexperienced taping or gradual loosening of the tape due to patient movement and/or sweating may cause the tape to lose its grip and fail in its function to maintain the needle, flow tube and coupling suitably anchored. It is also difficult to apply adhesive tape to a patient in a moving vehicle, i.e., an ambulance. Adhesive taping also takes time, i.e., in the range of 2 to 3 minutes. In an emergency, this may be too long a time.

The prior art includes various patents which attempt to stabilize intravenous apparatus. The approaches taken have been either very complicated requiring new intravenous apparatus designs, or have used simple clips to frictionally hold the tubing in place. The latter types have generally ignored the effects of patient movement on the needle section of the intravenous apparatus, and none address the problem of decoupling between needle and tubing. None of the prior art systems take into account the uniqueness of newer intravenous apparatus, such as the angio catheter systems presently in use. Angio catheter systems have a plastic over-needle tube inserted into the vein with attached hub to attach intravenous tubing. The prior art systems are difficult to use with these newer systems.

SUMMARY OF THE INVENTION

The present invention addresses the above problems by providing a very flexible type of system for holding intravenous apparatus. The present invention has the advantages of ease and speed in attachment of intravenous apparatus, i.e., 10 to 15 seconds, as opposed to the 2 to 3 minutes with prior art means. The present invention lends itself to the newer intravenous apparatus and is especially useful under stress situations such as ambulance use in the field. An added advantage is its ease of removal versus adhesive tape.

According to the present invention, an anchor pad is provided which has straps associated therewith for securing the pad to the arm, leg or the like of the patient. Attached to the top face of the pad are two latch arrangements for adjustably holding the tubing and needle sections of an intravenous apparatus in place. and needle sections of an intravenous apparatus in place.

Accordingly, it is a principal object of this invention to provide a novel and improved means for securing a needle and coupled flow tube to a patient.

It is another object of this invention to provide a novel and improved means for inhibiting separation of a flow tube from its coupling to a needle while such needle remains inserted in the vein of the patient.

It is a further object of the invention to provide an anchor pad strapped to the patient and having latch arrangements to secure, support and hold the tubing and needle of an intravenous apparatus and thereby prevent movement thereof which would dislodge or move the needle, or separate the needle from the coupling.

Other and further objects, as well as various advantages and features of novelty which characterize the invention are pointed out with particularity in the claims annexed hereto and forming a part hereof. However, for a better understanding of the invention, its advantages and objects obtained by its use, reference should be had to the drawings which form a further part hereof, and to the accompanying descriptive matter in which there is illustrated and described a preferred embodiment of the invention.

DETAILED DESCRIPTION OF THE INVENTION

Figure 1:
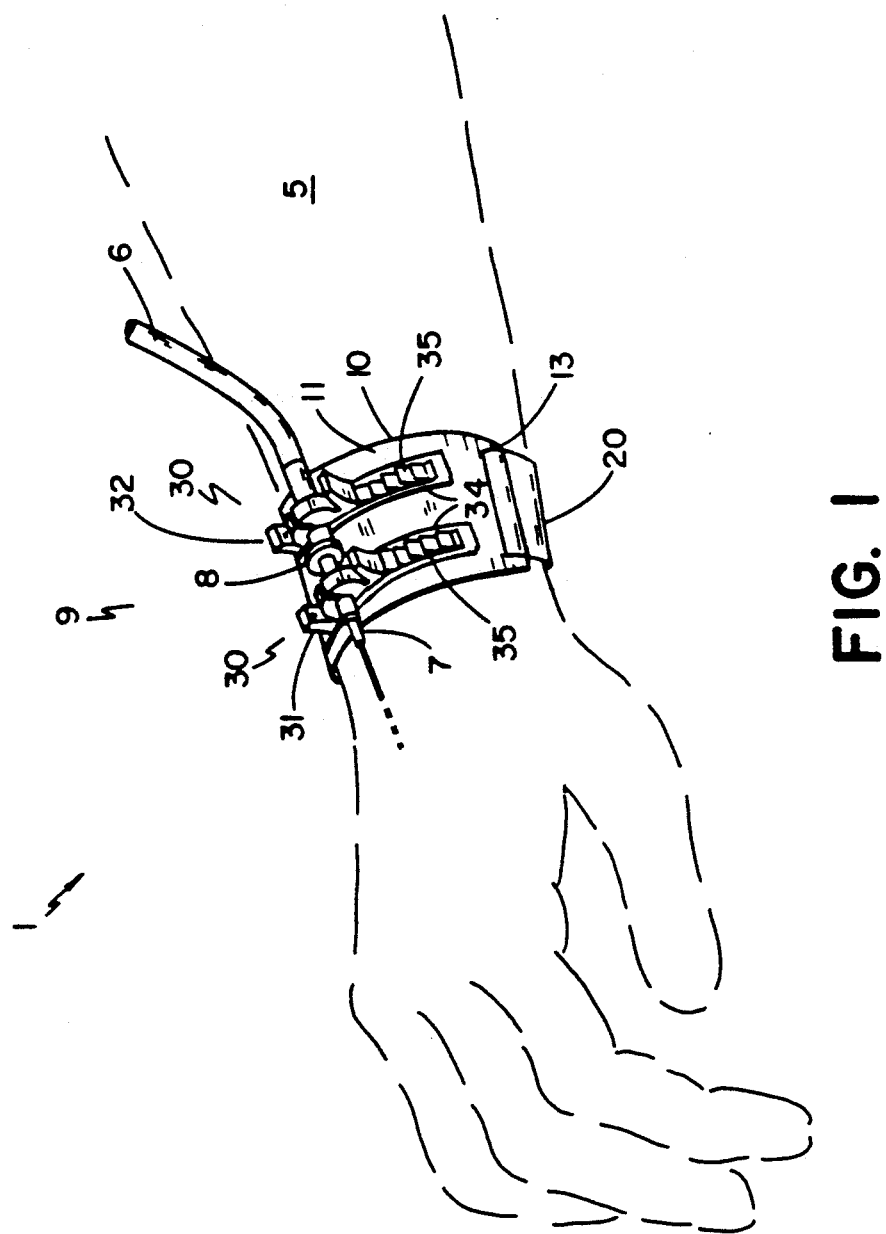
FIG. 1 is a perspective view of an intravenous apparatus holder constructed in accordance with the principles of my invention.
Figure 2:
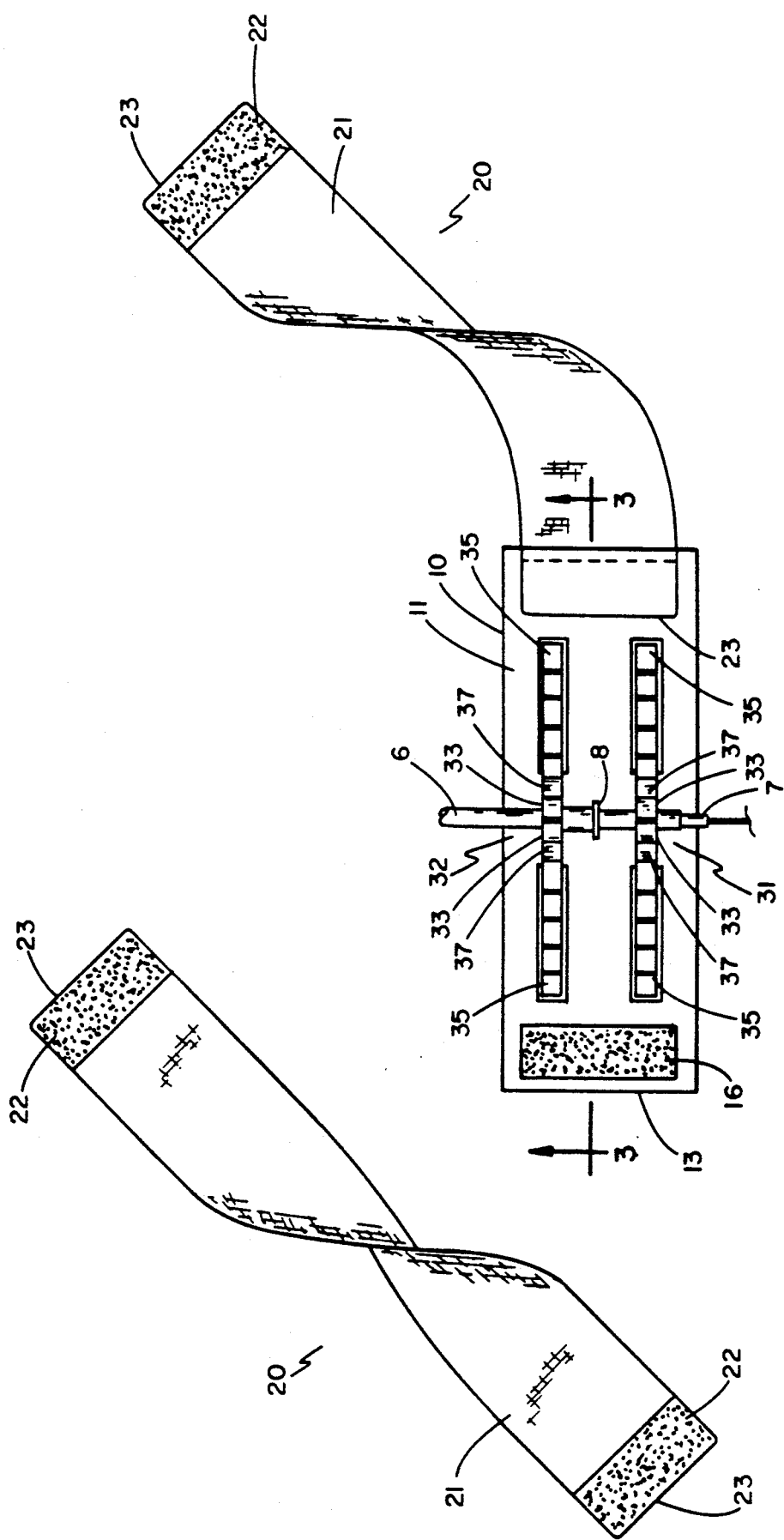
FIG. 2 is a top plan view of the holder illustrated in FIG. 1
Figure 3:
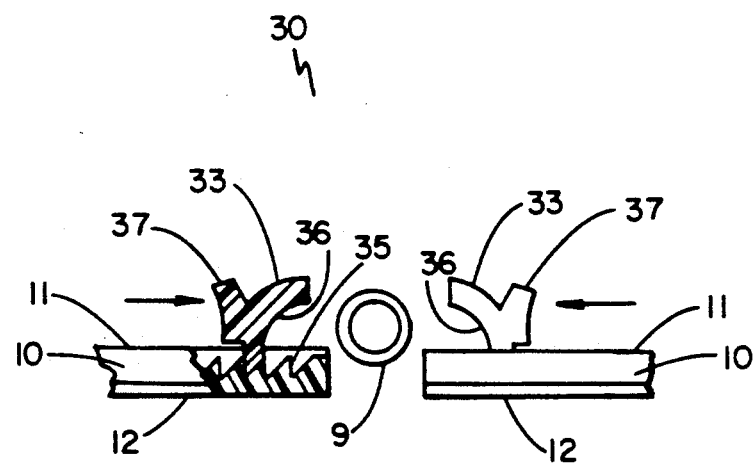
FIG. 3 is a fragmentary section taken along line 3—3 of FIG. 2 showing the holder in an open position.
Figure 4:
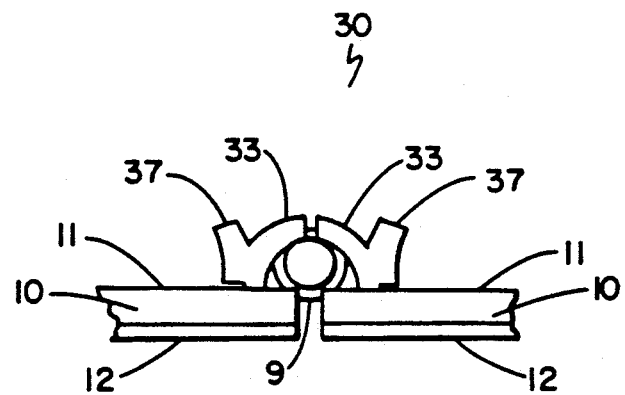
FIG. 4 is a section taken along line 3—3 of FIG. 2 showing the holder in a closed position.
Figure 5:
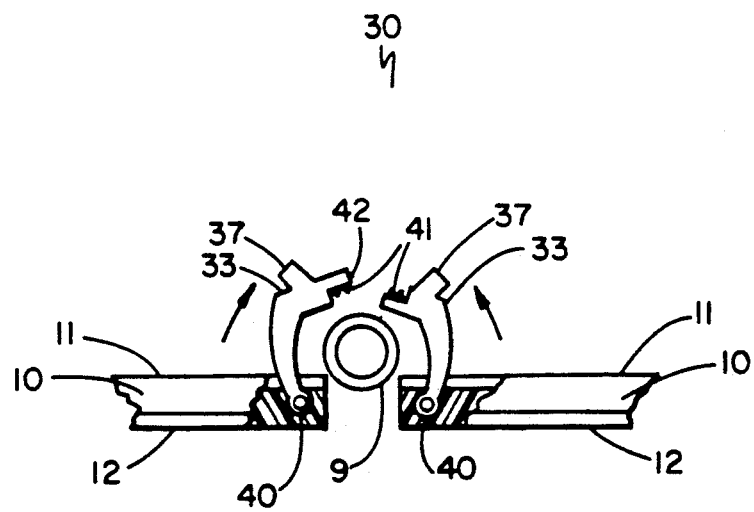
FIG. 5 is a section view along line 3—3 of FIG. 2 illustrating another embodiment of the invention constructed in accordance with the principles of my invention in the open position.
Figure 6:
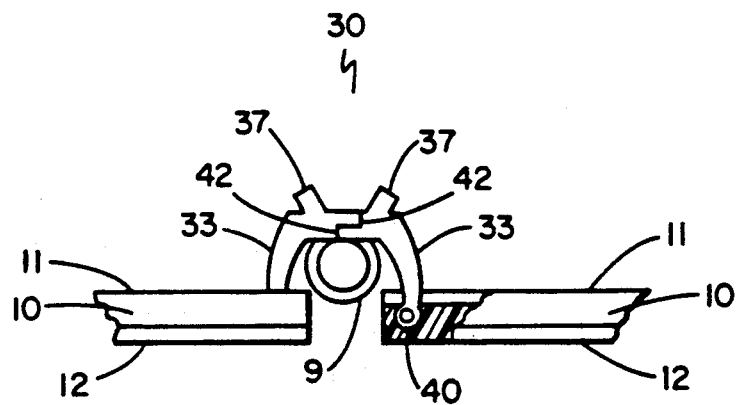
FIG. 6 illustrates the embodiment shown in FIG. 5 in the closed position.
Figure 7:
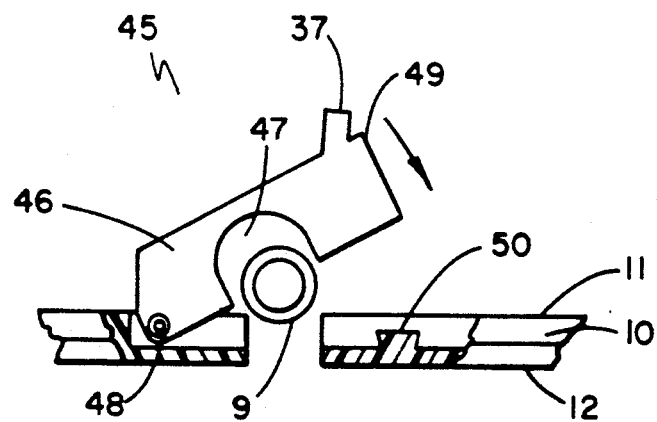
FIG. 7 is a section view along line 3—3 of FIG. 2 illustrating still another embodiment of the invention constructed in accordance with the principles of my invention in the open position.
Figure 8:
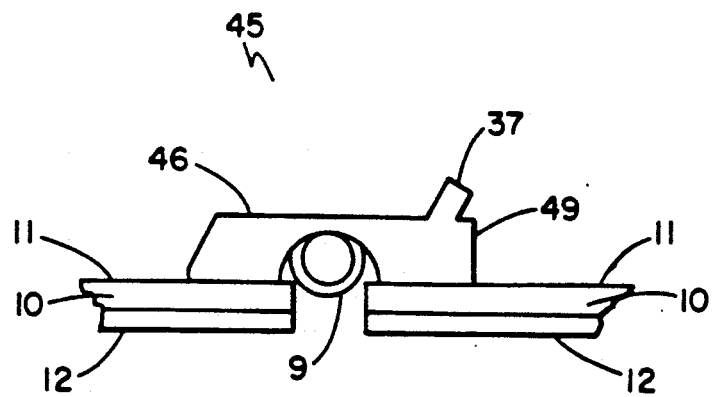
FIG. 8 illustrates the embodiment shown in FIG. 7 in the closed position.

Referring to the drawings in detail wherein like numerals indicate like elements, reference numeral 1 represents an intravenous apparatus holder constructed in accordance with the present invention. The intravenous apparatus 9 is comprised of a needle section 7 and a tubing section 6. The place where the tubing section 6 and needle section 7 join is indicated by reference numeral 8. The holder 1 is comprised generally of a pad 10 having an outer face 11, an under face 12, a strap 20 which affixes the pad 10 to a patient's arm 5, and two latch arrangements 30 joined to the pad's outer face 11 for holding the intravenous apparatus needle section 7 and tubing section 6 in place with respect to the patient's arm 5.

The pad 10 is made of a flexible material and in this embodiment has a generally rectangular shape. Other embodiments may use a different pad shape. The pad 10 is generally planar and provides relatively large surface area contact with the patient's limb 5 (in this example the limb is an arm) thereby providing a stable foundation for the holder 1. In one version of the invention, the pad's under face 12 has adhesive applied thereto. This invention version would be used where stability and a firm grasp of the intravenous apparatus 9 is desired. In the present embodiment of the invention linear Velcro strips 16 are attached to pad's outer face 11 in parallel and near to the pad's shorter sides 13. The strap 20 is comprised of two flat longitudinal pieces 21 with a Velcro section 22 near each piece end 23 on opposite sides. One end 23 of each piece 21 is attached by means of one of its end Velcro sections 22 to an individual pad outer face Velcro strip 16. The other piece ends 23 are attached to each other by means of the remaining Velcro sections 22. In this manner the pad 10 is firmly affixed on the patient's arm 5.

The two latch arrangements 30 are positioned in a line parallel to the pad's shorter sides 13 and approximately in the middle of the pad's outer face 11. The latch arrangements 30 are in line with the needle and tubing sections 7 and 6, respectively, of the intravenous apparatus 9. The forward latch arrangement 31 is used to hold the needle section 7 and the rearward latch arrangement 32 is used to hold the tubing section 6. The coupling 8 between needle 7 and tubing 6 is positioned between the forward 31 and rearward 32 latch arrangements. Each latch arrangement 30 has two holding elements 33 juxtaposed about the needle 7 or tubing 6 section to be held by the particular latch arrangement 31 or 32. Each holding element 33 is slid along a groove 34 in the pad's outer face 11 perpendicular to the pad's shorter sides 13. Each groove 34 has ratchet teeth 35 whereby the holding element 33 is prevented from moving back from the needle 7 or tubing 6 to be held. The holding elements 33 are arc-shaped with their concave sides 36 facing the needle 7 or tubing 6 to be held. To release the holding device 33 from its holding action and move it away from the needle 7 or tubing 6, downward pressure is placed on a tab 37 formed on each element 33 thereby causing the element 33 to be manually bent backward away from the needle 7 or tubing 6 and slid back across the ratchet teeth 35. The natural tendency of each holding element 33 is to rotate toward the needle 7 or tubing 6 to be held, thereby being held in place by the ratchet teeth 35.

In another embodiment of the holder 1 the latch arrangements 31 and 32 are comprised of hinged holding elements 33. The grooves 34 are eliminated. The holding elements 33 are hinged at one end 40 to the pad 10. The devices 33 are arc-shaped and rotate about their hinged ends 40 toward the needle 7 or tubing 6 sections. Locking teeth 41 are affixed to the non-hinged ends 42 of the holding elements 33. The locking teeth 41 of one holding element 33 interlocks with the locking teeth of the complementary holding element 33 juxtaposed on the other side of the needle 7 or tubing 6 to be held. In still another embodiment of the present invention the latch arrangements 31 and 32 are comprised of clamps 45. Each clamp 45 has a hinged arm 46 with a generally semi-circular opening 47 in its approximate midpoint, the opening 47 having an orientation toward the pad's outer face 11. One end 48 of the arm 46 is hinged to the pad 10. The clamps 45 are positioned perpendicularly to the pad's shorter sides 13 and close down on the needle 7 or tubing 6 in this perpendicular alignment. The opening 47 in the hinged arm 46 fits over the needle 7 or tubing 6. The clamp's nonhinged end 49 frictionally engages a post 50 whereby the clamp's hinged arm 46 is held in a closed position over the needle 7 or tubing 6 to be held.

It is understood that the above-described embodiments are merely illustrative of the application. Other embodiments may be readily devised by those skilled in the art which will embody the principles of the invention and fall within the spirit and scope thereof.

I claim:

1. A device for holding an intravenous apparatus with needle and tube sections to a patient's limb, comprising:
   a generally rectangular planar pad having four sides, the shorter sides of which are parallel to the general longitudinal axis of the intravenous apparatus when secured across the outer face of said pad, and having two faces, an outer face containing a forward and a rearward groove each of which is aligned perpendicular to the pad's shorter sides, and an under face for contacting the patient;
   a plurality of straps connected to said pad outer face near to said shorter pad sides for securing said pad to said patient's limb; and
   two separate latch arrangements, a forward one near to one pad longer side for holding said needle section and a rearward one near to the other longer side for holding said tubing section, attached to said pad outer face for adjustably holding said intravenous apparatus needle and tubing sections, said latch arrangements positioned parallel to the pad's longer sides and approximately in the middle of the pad's outer face, each said latch arrangement consisting of two holding elements positioned about and adapted for holding the needle and tubing sections, wherein said forward latch holding elements are slidably attached to said forward groove and said rearward latch holding elements are slidably attached to said rearward groove.

2. A device in accordance with claim 1 wherein:
   each groove has ratchet teeth whereby the holding element is prevented from moving back away from the needle or tubing section adapted to be held.

3. A device in accordance with claim 2 wherein:
   said holding elements are each formed into an arc-shape beginning with a lower section coacting with said ratchet teeth and an upper section having its concave side for facing the needle or tubing section adapted to be held.

4. A device in accordance with claim 3 wherein:
   said holding elements are pivotally positioned in said grooves so that each may be manually pivoted away from the needle or tubing section adapted to be held.

5. A device in accordance with claim 4 wherein:
   each holding element disengages from the ratchet teeth when manually pivoted away from the needle or tubing section adapted to be held.

6. A device in accordance with claim 5 wherein:
   said under face has adhesive applied thereto.

7. A device for holding an intravenous apparatus with needle and tube sections to a patient's limb, comprising:
- a generally rectangular planar pad having four sides, the shorter sides of which are parallel to the general longitudinal axis of the intravenous apparatus when secured across the outer face of said pad, and having two faces, an outer face, and an under face for contacting the patient;
- a plurality of straps connected to said pad outer face near to said shorter pad sides for securing said pad to said patient's limb; and
- two separate latch arrangements, a forward one near to one pad longer side for holding said needle section and a rearward one near to the other longer side for holding said tubing section, attached to said pad outer face for adjustably holding said intravenous apparatus needle and tubing sections, said latch arrangements positioned parallel to the pad's longer sides and approximately in the middle of the pad's outer face, each said latch arrangement consisting of two hinged holding elements positioned about and adapted for holding the needle and tubing sections, wherein each hinged element has two ends one of which is attached to the pad outer face and the other end of which is pivotable over the said needle or tubing section.

8. A device in accordance with claim 7 wherein:
said holding elements are arc-shaped with their concave sides facing the needle or tubing section adapted to be held.

9. A device in accordance with claim 8 wherein:
said holding elements rotate about their hinged ends toward the needle or tubing sections adapted to be held.

10. A device in accordance with claim 9 wherein:
locking teeth are affixed to the non-hinged ends of said holding elements whereby the locking teeth of one holding element in a latch arrangement interlocks with the locking teeth of the other holding element in the same latch arrangement.

11. A device in accordance with claim 10 wherein:
said under face has adhesive applied thereto.

* * * * *